US00PP18404P3

(12) United States Plant Patent
Jensen

(10) Patent No.: US PP18,404 P3
(45) Date of Patent: Jan. 8, 2008

(54) MINIATURE ROSE PLANT 'JENTHREE'

(50) Latin Name: *Rosa hybrida*
Varietal Denomination: JENthree

(76) Inventor: Svend Jensen, Kongensgade 32, Christiansfeld (DK), 6070

( * ) Notice: Subject to any disclaimer, the term of this patent is extended or adjusted under 35 U.S.C. 154(b) by 203 days.

(21) Appl. No.: 11/170,518

(22) Filed: Jun. 29, 2005

(65) Prior Publication Data

US 2007/0006354 P1 Jan. 4, 2007

(51) Int. Cl.
*A01H 5/00* (2006.01)

(52) U.S. Cl. ..... Plt./121

(58) Field of Classification Search ..... Plt./121, Plt./122

See application file for complete search history.

*Primary Examiner*—Howard J. Locker
(74) *Attorney, Agent, or Firm*—Venable LLP

(57) ABSTRACT

A new miniature rose plant which has abundant, long lasting, pink colored flowers and attractive foliage. The variety successfully propagates from softwood cuttings and is suitable for year round production in commercial glass houses as a flowering pot plant. This new and distinct variety has shown to be uniform and stable in the resulting generations from asexual propagation.

2 Drawing Sheets

Latin name of genus and species: *Rosa hybrida* 'JENthree'.

Variety denomination: The new variety is named 'JENthree'.

BACKGROUND OF THE INVENTION

The present invention constitutes a new and distinct variety of miniature rose plant, which was developed by artificially pollinating an unnamed seedling (not patented in the US) with an unnamed seedling (not patented in the US). The two parents were crossed during the summer of 2001, and the resulting seed was sown in December 2001, in a controlled glasshouse environment. Out of the resulting seedlings one seedling was selected, as a distinct new variety and was named 'JENthree'.

The variety can be distinguished from its seed parent, an unnamed seedling, by the following combination of characteristics:

- 'JENthree' has medium sized double flowers, while the unnamed seed parent has large double flowers.
- 'JENthree' has pink colored petals, while the unnamed seed parent has red petals.

The new variety can be distinguished from its pollen parent, an unnamed seedling created by the same inventor, by the following combination of characteristics:

- 'JENthree' has bigger flowers and foliage as compared to the unnamed pollen parent.
- 'JENthree' has pink colored petals, while the unnamed pollen parent has dark red petals.

BRIEF SUMMARY OF THE INVENTION

Initial asexual reproduction of 'JENthree' by cuttings was first carried out by the inventor in Christiansfeld, Denmark. The reproduction was conducted under controlled greenhouse conditions. Having thus demonstrated asexual reproduction it was found that all characteristics and distinctions came true to form and were established in succeeding propagations. 'JENthree' is a low and compact miniature rose with medium vigor.

The objective of the hybridization of this rose variety for commercial greenhouse culture was to create a new and distinct variety with:

- Uniform and abundant flowers with good keeping properties;
- Attractive long lasting foliage and compact growth;
- Year round flowering under glasshouse conditions;
- Suitability for production from softwood cuttings in pots;
- Durable flowers and foliage which make the variety suitable for distribution in the floral industry.

This combination of qualities was not present in previously available commercial cultivars of this type and distinguish 'JENthree' from all other varieties of which the inventor is aware. The seeds from hybridization were planted in a controlled environment and evaluations were conducted on the resulting plants. 'JENthree' was selected by Svend Jensen, in his development program in Christiansfeld, Denmark.

BRIEF DESCRIPTION OF THE DRAWINGS

The accompanying color illustrations show as true as is reasonable to obtain in color photographs of this type, the typical characteristics of the buds, flowers, leaves, stems of 'JENthree'. Specifically illustrated in:

Photo Sheet 1

Figure 1:
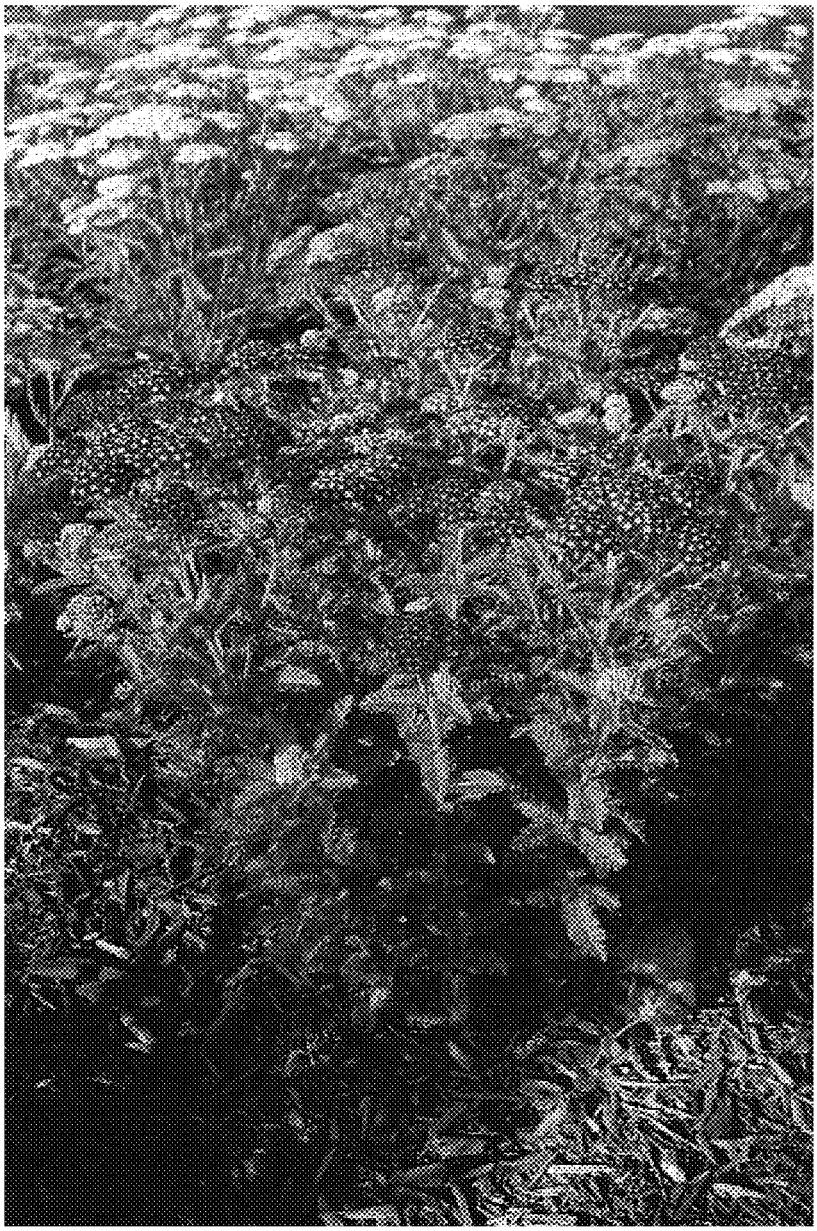
Figure 2:
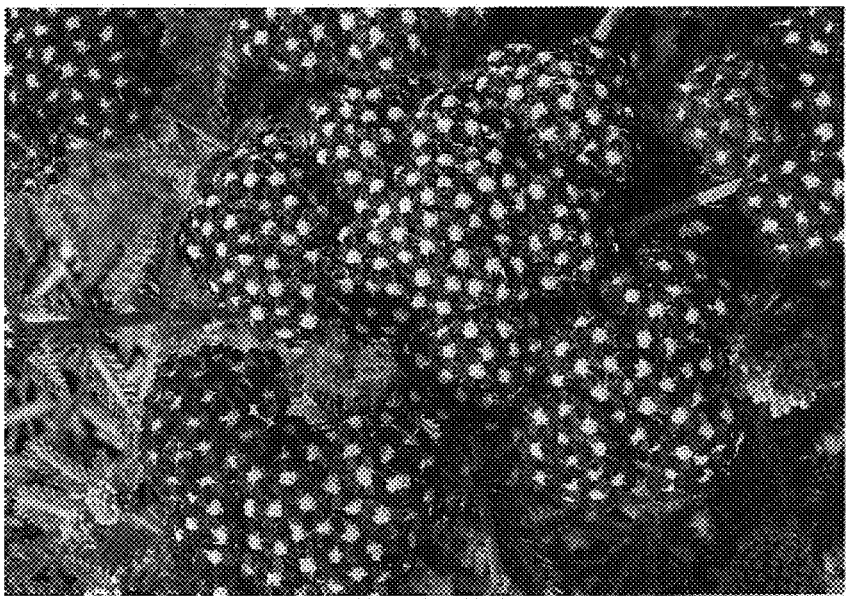
Figure 3:
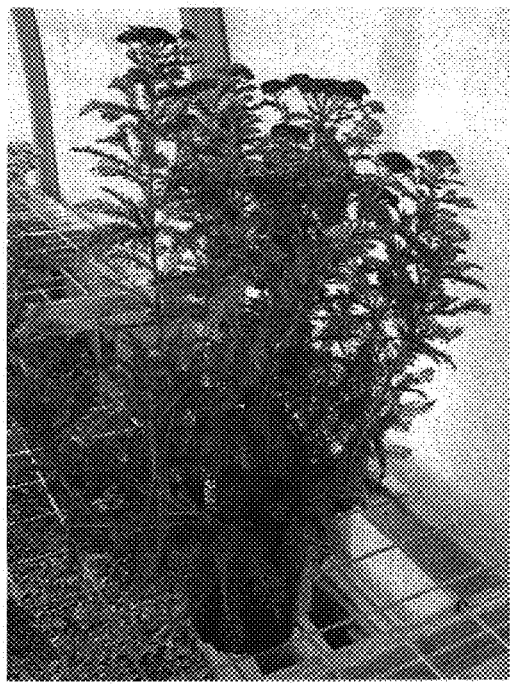

1: Young shoot.
2: Bud before opening of the sepals.
3: Bud at the stage of opening of the sepals.
4: Bud at the stage of opening the petals.
5: Flower during course of opening.
6: Open flower—plan view—obverse.

7: Open flower—plan view—reverse.

8: Fully open flower—plan view—obverse.

9: Fully open flower—plan view—reverse.

Photo Sheet 2

10: Receptacle showing stamens and pistils.

11: Receptacle showing pistils (stamens and sepals removed).

12: Flower petals, detached—inner surface.

13: Flower petals, detached—outer surface.

14: Bare stem exhibiting thorns and flower attachment.

15: Three leaflets upper side.

16: Three leaflets reverse side.

17: Five leaflets upper side.

18: Five leaflets reverse side.

DETAILED BOTANICAL DESCRIPTION OF THE VARIETY

The following is a detailed description of the Miniature Rose: *Rosa hybrida* 'JENthree'.

The following observations, measurements, values and comparisons describe plants grown in glass houses in Christiansfeld, Denmark. The age of the observed plants was 11 to 13 weeks after propagation by cuttings and growth as a flowering pot plant in container of 10 centimeters diameter.

Environmental conditions in the cultivation area for the observed plants ranged from 64 to 78 degrees Fahrenheit and 10 to 20 hours of light per day. Light levels ranged from 600 foot candle to 6000 foot candles. The relative humidity ranged from 50 to 85%. Bonzi® brand growth regulator (R',R'-beta-[(4-chlorophenyl)methyl]-alpha(1,1-dimethylethyl)-1H-1,2,4-triazole-1-ethanol) was used to keep the plant shape compact. The growth regulator concentration was titrated according to the label directions. The plant was not systematically observed without this growth regulator.

Color references are made using The Royal Horticultural Society (London, England) Colour Chart, 1995, except where common terms of color are used.

For a comparison, the nearest existing rose variety is 'POULrolyt', a rose variety described and illustrated in U.S. Plant Pat. No. 13,138.

Chart 1 details several physical characteristics of 'JENthree' and 'POULrolyt'.

CHART 1

| | 'JENthree' | 'POULrolyt' |
|---|---|---|
| Petal color, Upper surface | Red Group 50C | Red Group 50A |
| Petal color, Reverse surface | Red Group 50C | Red Group 58B |
| Petal count | 40 | 30-35 |

Parents:

*Seed parent.*—Unnamed seedling.

*Pollen parent.*—Unnamed seedling.

Classification:

*Botanical.*—*Rosa hybrida.*

*Commercial.*—Miniature.

Plant:

*Plant growth.*—Moderately vigorous. Growth is compact — upright to bushy. When grown in a 10 cm pot, the average height of the plant itself is 18 to 20 cm, and average width is 20 cm. When grown as in a 15 cm pot, the average height of the plant itself is 22 to 27 cm, and average width is 30 cm.

Production time is generally 11 to 13 weeks depending on average temperature, light level, and cultural practices.

Stem:

*Color.*—Young wood: Yellow-Green Group 146 B. (With intonations of Greyed-Purple Group 183D). Older wood: Yellow-Green Group 147 B. (With intonations of Greyed-Purple Group 183D).

*Thorns.*—Incidence: 6–8 thorns per stem. Size: 2-3 mm. Color: Greyed-Purple Group 183D. Shape: Deep concave.

*Surface.*—Young wood: Smooth. Older wood: Smooth.

*Stem.*—Diameter: 2–3 mm. Internode: 20–30 mm in length. Numbers of internodes: 5–6.

Plant foliage: Leaves arranged alternately, compound with 3 to 5 leaflets per leaf, generally symmetrical, abundant, and flat in aspect with stipules at petiole base.

*Quantity of leaves.*—5–6 per lateral branch.

*Leaf size.*—Medium 40–60 mm (l). by 30–40 mm (w), for five leaflets.

*Petioles.*—Color: Yellow-Green Group 147 A, (With intonations of Greyed-Purple Group 183D). Margins: Entire. Length: 5–7 mm. Diameter: About 0.5–1 mm.

*Stipules.*—Size: 7-10 mm. Surface: Smooth. Color: Yellow-Green Group 147A–B. Margins: Entire.

*Rachis.*—Color: Yellow-Green Group 147A (With intonations of Greyed-Purple Group 183D). Margins: Entire. Length: 10 to 20 mm. Diameter: 0.5–1 mm.

*Leaflets.*—Edge: Serrated. Serration: Single. Shape: Ovate with acute apex and obtuse base. Texture: Smooth. Appearance: Dull. Size: Length: 15 to 30 mm; width: 8 to 15 mm.

*Color.*—Young foliage: Upper surface: Yellow-Green Group 147B (with intonations of Greyed-Purple Group 183D). Lower surface: Greyed-Green Group 189A (with intonations of Greyed-Purple Group 183D). Mature foliage: Upper surface: Yellow-Green Group 147A (with intonations of Greyed-Purple Group 183D). Lower surface: Greyed-Green Group 191A (with intonations of Greyed-Purple Group 183D).

*Leaf vein color.*—Upper surface: Yellow-Green Group 147A. Lower surface: Greyed-Green Group 192D.

Inflorescence:

*Blooming habit.*—Recurrent.

*Number of flowers.*—Generally 3–5 buds per flowering stem.

*Peduncle.*—Color: Yellow-Green Group 147B–C. Texture: Smooth. Length: 10–20 mm. Orientation: Upright.

*Receptacle.*—Surface: Smooth, glabrous. Shape: Funnel-shaped. Size: 5–6 mm (h) by 5–6 mm (w). Color: Yellow-Green Group 147C.

*Sepals.*—Number: 5. Shape: Narrowly Ovate with acute tips. Texture: Leathery. Margin: Foliaceous appendages on two of the five sepals. Appearance: Dull. Color: Upper surface: Yellow-Green Group 147A–B. Reverse surface: Greyed-Green Group 191D. Size: 20 mm (l), by 5 mm (w).

*Buds.*—Size: 15–20 mm (h) by 10–12 mm (w) upon opening. Shape: Ovoid. Color: Red Group 50C (at ¼ open).

*Flower duration.*—As a pot plant, flowers in flushes which last from 17 to 19 days.

*Fragrance.*—None.

*Flower size.*—40–50 mm in diameter and 14–17 mm in height.

*Flower form* (*shape viewed from the side*).—Part open: Cup shaped. Open: Flat.

*Flower color.*—Petals, during opening: Upper surface: Red Group 50C; Reverse surface: Red Group 50C. Petals after opening: Upper surface: Red Group 50C; Reverse surface: Red Group 50C (with intonations of White Group 155D).

*Basal petals spots.*—Size: 1–3 mm. Color: White Group 155D.

*General tonality.*—On Open flower: Third day: Red Group 50C; Afterwards: Red Group 50C.

*Petals.*—Petal reflex: Outermost petals reflex backwards during opening. When fully open: all petals reflex backwards. Texture: Smooth. Petal edge: Entire. Petal count: Approximately 40 on average per flower. Petal size: 15–20 mm (l) by 10–20 mm (w). Shape: Outer petals: Round; Inner petals: Ovate; Apex: Orbicular; Base: Obtuse to rotundate.

*Reproductive organs.*—Stamen number: Approximately 40 on average per flower. Stamens length: 4–5 mm. Pollen Color: Yellow-Orange Group 22B. Pollen Abundance: High. Anther Size: 1–1.5 mm (l). Anther Color: Yellow-Orange Group 22D. Anther Shape: Oblong. Filament Size: 3–4 mm (l). Filament Color: White Group 155D. Pistils number: Approximately 25 on average per flower. Stigma Location: Inferior location relative to anthers. Stigma Color: Green-White Group 157D. Style Color: Green-White Group 157D (with intonations of Greyed-Purple Group 187D). Style Length: 1 to 2 mm.

Development:

*Vegetation.*—Dense.

*Blooming.*—Abundant.

*Fruit set.*—None observed.

*Disease resistance.*—Above average resistance to mildew and Botrytis under normal growing conditions in Christiansfeld, Denmark.

*Hips/seeds.*—Fruits have not been observed because the plant has never been grown to the stage of seed development because the variety is developed for use as a flowering pot plant only.

*Winter hardiness & drought/heat tolerance.*—Not evaluated because the variety is a potted flowering plant, developed for a one time use only.

It is claimed:

1. A new and distinct variety of rose plant of the miniature class, substantially as herein illustrated and described as a distinct and novel rose variety due to its abundant, long lasting, pink colored flowers, attractive long lasting foliage, vigorous and compact growth, year round flowering under glasshouse conditions, suitability for production from softwood cuttings in pots, and durable flowers and foliage which make the variety suitable for distribution in the floral industry.

* * * * *